United States Patent [19]

Hegasy et al.

[11] Patent Number: 4,562,069
[45] Date of Patent: Dec. 31, 1985

[54] TWO-PHASE FORMULATION

[75] Inventors: Ahmed Hegasy, Leverkusen; Roland Rupp, Leichlingen; Klaus-Dieter Rämsch, Wuppertal; Helmut Luchtenberg, Niederkassel, all of Fed. Rep. of Germany

[73] Assignee: Bayer Aktiengesellschaft, Leverkusen, Fed. Rep. of Germany

[21] Appl. No.: 606,104

[22] Filed: May 2, 1984

[30] Foreign Application Priority Data

May 21, 1983 [DE] Fed. Rep. of Germany ....... 3318649

[51] Int. Cl.[4] .................. A61K 31/79; A61K 31/455; A61K 47/00
[52] U.S. Cl. ...................................... 424/80; 514/356; 514/772; 514/781; 514/784; 514/788; 424/19; 424/22
[58] Field of Search ............................ 424/80, 19, 22; 514/356, 772, 781, 784, 788

[56] References Cited

U.S. PATENT DOCUMENTS 4,343,789  8/1982  Kawata et al. .......................... 424/19
4,404,183  9/1983  Kawata et al. .......................... 424/19
4,412,986 11/1983  Kawata et al. .......................... 424/80

FOREIGN PATENT DOCUMENTS

| 47899 | 3/1982 | European Pat. Off. . |
| EP78430 | 5/1983 | European Pat. Off. . |
| 2822882 | 12/1978 | Fed. Rep. of Germany . |
| 3024858 | 1/1981 | Fed. Rep. of Germany . |
| 3142853 | 5/1983 | Fed. Rep. of Germany . |
| 54-46837 | 4/1979 | Japan . |
| 56-68619 | 6/1981 | Japan . |
| 56-110612 | 9/1981 | Japan . |
| 57-85316 | 5/1982 | Japan . |
| 57-167911 | 10/1982 | Japan . |
| 58-77811 | 5/1983 | Japan . |

OTHER PUBLICATIONS

Sugimoto et al., C.A. 95, #86250c (1981) of Chem. Pharm. Bull. 29(6): 1715-23, (1981).
Sugimoto et al., C.A. 96, #110072q (1982) of Iyakuhin Kenkyu 12(4): 988-992, (1981).
Sugimoto et al., C.A. 95, #53922d (1980) of Drug Dev. Ind. Pharm. 6(2): 137-160, (1980).
Sugimoto et al., C.A. 98, #132212d (1983) of Chem. Pharm. Bull. 30(12): 4479-88, (1982).

*Primary Examiner*—Shep K. Rose
*Attorney, Agent, or Firm*—Sprung Horn Kramer & Woods

[57] ABSTRACT

In the treatment of cardiovascular and coronary disorders by administering to a patent suffering therefrom a solid preparation comprising nifedipine, the improvement which comprises administering such nifedipine in the form of a solid two-phase medicament formulation comprising a nifedipine coprecipitate, in which the nifedipine is present in a non-crystalline form, and crystalline nifedipine, whereby the nifedipine rapidly enters the blood stream in a relatively high concentration which is maintained for a relatively long time.

9 Claims, No Drawings

TWO-PHASE FORMULATION

The invention relates to special solid medicament formulations containing nifedipine, a process for their preparation and their use as cardiovascular agents.

It has already been disclosed that the compound nifedipine has potent cardiovascular effects, especially coronary and antihypertensive effects (compare British Pat. No. 1,173,862). By reason of the poor solubility and high sensitivity to light of nifedipine, relatively severe difficulties occur in pharmaceutical processing, as is obvious from numerous publications and patent applications on special formulations of this active compound. For example, to utilize the coronary effect of nifedipine, gelatin capsules which contain nifedipine in the dissolved form and which ensure a rapid onset of action have been produced (compare U.S. Pat. No. 3,784,684). The rapid onset of action necessary for coronary disease is ensured by this capsule formulation. A disadvantage of this formulation with a rapid onset of action is the short duration of action. The concentration of nifedipine in the plasma decreases only 3 hours after administration to about 1/10 of the maximum initial concentration. Thus, for long-term treatment of coronary and hypertensive patients, it is necessary to administer the capsules repeatedly at short intervals.

Solid nifedipine formulations which are described and claimed in, for example, British Pat. No. 1,456,618 ("solid solution in polyethylene glycol") or in European Published Specification No. 1,247 also have the same disadvantage of the short duration of action. In addition, an attempt is made in DE-OS (German Published Specification) No. 2,822,882 to compensate for the poor solubility of nifedipine, using certain solubilizers and surface-active substances. All these formulations of nifedipine have the disadvantage of a short duration of action. The use of additional auxiliaries, such as solubilizers, surface-active substances and porous vehicles, frequently leads to forms for administration which are very bulky and can be taken by the patient only with difficulty.

Furthermore, it is desirable to keep the number and the amount of the auxiliaries and vehicles as low as possible, since, when comparing two medicament preparations, preference is always given to that preparation which contains as few auxiliaries as possible in addition to the active compound, in order substantially to avoid undesired biological effects.

Attempts have also been made to produce nifedipine formulations having a longer duration of action. These contain nifedipine in a crystalline form (compare DE-OS (German Published Specification) No. 3,039,919). In this reference, an attempt is made, by selecting a particular crystal size, to improve the release of nifedipine in aqueous media and thus to increase the absorbability and bioavailability on oral administration. It is true that the resulting tablets have a markedly longer action, which persists for more than 8 hours, but they have the disadvantage that the onset of action is considerably delayed. An onset of action after a few minutes is desirable for the acute treatment of coronary disease.

In order to utilise as completely as possible the advantageous properties of nifedipine, a need as long existed to make available a homogeneous formulation which
(a) has a very rapid onset of action, particularly for the acute treatment of coronary disease;
(b) has a long duration of action, particularly for the treatment of hypertension and for long-term therapy;
(c) can be produced without an elaborate pharmaceutical process;
(d) is a small form for administration having a high content of active compound, which can reliably and easily be taken by the patient.

The present invention relates to solid two-phase medicament formulations containing a combination of a nifedipine coprecipitate, in which the nifedipine is present in a dissolved, non-crystalline form, and a proportion of crystalline nifedipine.

Solid two-phase medicament formulations, such as tablets, coated tablets, capsules or sachets, containing a combination of nifedipine coprecipitate, in which 1 part by weight of nifedipine is present in 1 to 10, in particular 2 to 6, parts by weight of coprecipitate former, and a proportion of 1 to 5 parts by weight of crystalline nifedipine are preferred.

Solid two-phase medicament formulations of this type in the form of tablets or coated tablets are particularly preferred.

Suitable and preferable as the coprecipitate former are polyvinylpyrrolidone (PVP), methylcellulose, hydroxypropylcellulose and hydroxypropylmethylcellulose, especially PVP.

Nifedipine crystals which have a mean particle diameter of about 10 to 1 $\mu$m, or nifedipine crystals which have a specific surface area of 0.5 to 6 $m^2/g$, in particular 1.0 to 4 $m^2/g$, are preferably employed as the proportion of crystalline nifedipine.

The nifedipine coprecipitate is prepared by dissolving nifedipine and the coprecipitate former in a suitable organic solvent. Examples of suitable solvents are chlorinated lower hydrocarbons, such as, for example, methylene chloride and chloroform, acetone and lower aliphatic alcohols, such as, for example, ethanol, isopropanol or mixtures thereof. After solution is complete, the solvent is removed by means of a suitable drying process (for example vacuum drying or spray drying) and the remaining solid coprecipitate is then comminuted.

In addition, in a variant of this process, it is possible immediately to granulate further the solution of nifedipine and coprecipitate former in the organic solvent with suitable pharmaceutical auxiliaries and vehicles, and then to remove the organic solvent from the granules or powderrs by, for example, drying.

Examples of auxiliaries and vehicles which may be mentioned are: water, vegetable oils (for example groundnut/sesame oil), alcohols (for example ethyl alcohol and glycerol), glycols (for example propylene glycol and polyethylene glycol), solid vehicles, such as, for example, ground natural minerals (for example kaolins, clays, talc, chalk and Ca phosphate), ground synthetic minerals (for example highly disperse silicic acid and silicates), sugars (for example sucrose, lactose and glucose), emulsifying agents, such as non-ionic and anionic emulsifiers (for example polyoxyethylene fatty acid esters, polyoxyethylene fatty alcohol ethers, alkylsulphonates and arylsulphonates), dispersing agents, for example cellulose or cellulose derivatives such as methylcellulose, sodium carboxymethylcellulose, starch, lactose, PVP and crosslinked PVP, and lubricants (for example magnesium stearate, talc, stearic acid and sodium lauryl sulphate).

The crystalline nifedipine to be used according to the invention is prepared by milling the nifedipine crystals obtained on synthesis. This milling is preferably carried out with hammer mills or pinned disc mills, it being possible to obtain the desired particle size by varying the speed of rotation of the mill, the amount of product being introduced and/or the milling time.

It is advantageous for the preparation of particularly fine nifedipine crystals (particle diameter about 1 μm) to employ air jet mills.

The particle size is determined by measuring the specific surface area by the gas adsorption method (compare S. Brunauer: The absorption of gases and vapors, Princeton (1945)).

Knowing the state of the art and knowing the need, which has existed for years, to find a formulation which has both a rapid onset of action and a long duration of action of this active compound nifedipine, which is difficult to formulate, it is extremely surprising that a very simple and effective pharmaceutical arrangement, which places the specialist in the position of being able to utilize the coronary and hypotensive effects of nifedipine to an optimal extent, has been found in the combination according to the invention. The investigations which follow show that the formulation according to the invention combines at the same time the known advantageous properties of the nifedipine gelatin capsule (rapid mobilization of the active compound) with the retard effect lasting several hours (long-lasting levels in the blood plasma).

One two-phase tablet according to Example 1, containing 10 mg of nifedipine, of the coprecipitate and 20 mg of crystalline nifedipine, was administered orally to each of five healthy male subjects. Table 1 shows the concentration (μg/l) of nifedipine in the plasma over a period of 8 hours).

TABLE 1

| | Plasma concentration (μg/l) after administration of the two-phase tablet (according to Example 1) | | | | | | | | | |
|---|---|---|---|---|---|---|---|---|---|---|
| Subj. | 0.00 h | 0.25 h | 0.50 h | 0.75 h | 1.00 h | 1.50 h | 2.00 h | 3.00 h | 4.00 h | 8.00 h |
| 1 | <2 | <2 | 6.43 | 9.07 | 41.49 | 100.35 | 121.35 | 73.79 | 58.98 | 23.81 |
| 2 | <2 | 2.81 | 56.03 | 103.42 | 101.42 | 102.10 | 93.87 | 87.85 | 59.00 | 20.83 |
| 3 | <2 | <2 | 19.14 | 76.74 | 90.96 | 97.76 | 95.36 | 80.12 | 52.68 | 21.83 |
| 4 | <2 | <2 | 16.54 | 51.03 | 115.36 | 133.08 | 126.55 | 92.77 | 80.76 | 33.86 |
| 5 | <2 | 9.32 | 95.06 | 128.20 | 150.22 | 142.00 | 118.46 | 86.52 | 60.78 | 28.33 |
| X̄ | <2 | 3.03 | 38.64 | 73.69 | 99.89 | 115.06 | 111.12 | 84.21 | 62.44 | 25.73 |

TABLE 2

| | Plasma concentration (μg/l) after administration of a tablet containing 20 mg of crystalline nifedipine | | | | | | |
|---|---|---|---|---|---|---|---|
| Subj. | 0.00 h | 0.50 h | 1.00 h | 2.00 h | 3.00 h | 4.00 h | 8.00 h | 24.00 h |
| 1 | <2 | 10.73 | 16.15 | 16.55 | 28.19 | 29.29 | 11.93 | 7.02 |
| 2 | <2 | 8.11 | 24.75 | 27.34 | 26.84 | 24.04 | 16.62 | 3.20 |
| 3 | <2 | 10.92 | 31.16 | 25.14 | 18.83 | 16.03 | 11.02 | 6.41 |
| 4 | 5.21 | 11.42 | 17.73 | 18.93 | 56.48 | 27.75 | 17.32 | 8.91 |
| 5 | 2.11 | 21.35 | 28.25 | 19.84 | 20.84 | 27.95 | 11.67 | 6.71 |
| X̄ | 2.06 | 12.51 | 23.61 | 21.57 | 30.24 | 25.01 | 13.70 | 6.45 |

The same group of five healthy subjects received orally a tablet which contained 20 mg of nifedipine in the crystalline form. The plasma concentrations show a delayed onset of action and overall lower plasma concentrations (Table 2, see page 7).

The comparison experiments above show that the combined two-phase formulation according to the invention combines the advantages of various formulations hitherto known without having their specific disadvantages. By having this formulation, the specialist is placed in a position of being able to utilize the valuable coronary and hypotensive properties of the active compound nifedipine. The two-phase formulation permits simple, reliable and easy administration, and is an enrichment of pharmacy.

Medicament formulations which may be mentioned as being preferred for the combined two-phase system are: tablets, coated tablets, granules, capsules, suppositories, sachets and other solid medicament formulations. In certain cases, it can also be advantageous to combine the two-phase formulation according to the invention with other active compounds (for example with beta-blockers).

An advantageous method of preparation comprises initially preparing a nifedipine coprecipitate in the form of granules (granules I) and in a second step, preparing granules II which contain crystalline nifedipine and the mixing granules I and II in the ratio of amounts according to the invention and compressing to produce a suitable form for administration, such as, for example, tablets or coated tablets, or filling into hard gelatin capsules.

The exemplary embodiments which follow illustrate the invention.

EXAMPLE 1

Granules I 10 g of nifedipine and 40 g of polyvinylpyrrolidone (PVP) 25 are dissolved in 60 g of acetone, and this solution is granulated with a mixture of 105 g of microcrystalline cellulose, 20 g of corn starch and 10 g of crosslinked PVP. The composition is dried in vacuo, and then screened and mixed with 20 g of corn starch, 14.6 g of crosslinked PVP and 0.4 g of magnesium stearate.

Granules II 20 g of nifedipine, 34.8 g of microcrystalline cellulose, 12 g of corn starch and 10 g of lactose are mixed and granulated with a paste of 2 g of corn starch in water with the addition of 1 g of polyoxyethylene sorbitan monooleate (Twenn 80). The moist composition is dried and screened and mixed with 0.2 g of magnesium stearate.

Granules I and II are mixed and an amount of 300 mg is filled into hard gelatin capsules or compressed to produce tablets.

EXAMPLE 2

Granules I 50 g of nifedipine and 100 g of PVP 25 are dissolved in 350 g of acetone, and this solution is granulated with a mixture of 420 g of microcrystalline cellulose, 99.5 g of corn starch and 25 g of crosslinked PVP. The compositon is dried and screened.

Granules II 150 g of nifedipine are mixed with 150 g of microcrystalline cellulose and 180 g of corn starch and granulated with a paste of 22.5 g of corn starch in water. The moist composition is dried and screened.

Granules I and II are mixed with 100 g of crosslinked PVP and 3 g of magnesium stearate, and an amount of 130 mg is filled into hard gelatin capsules or compressed to produce tablets.

EXAMPLE 3

Granules I 100 g of nifedipine and 400 g of PVP 25 are dissolved in 750 g of acetone, and this solution is granulated with a mixture of 800 g of microcrystalline cellulose, 161 g of maize starch and 200 g of crosslinked PVP. The composition is dried and screened.

Granules II 100 g of nifedipine are mixed with 100 g of microcrystalline cellulose and 120 g of corn starch and granulated with a paste of 14 g of corn starch in water with the addition of 1 g of polyoxyethylene sorbitan monooleate. The moist composition is dried and screened.

Granules I and II are mixed with 200 g of cross-linked PVP and 4 g of magnesium stearate, and an amount of 220 mg is filled into hard gelatin capsules or compressed to produce tablets.

EXAMPLE 4

Granules I 100 g of nifedipine and 1,000 g of hydroxypropylmethylcellulose are dissolved in 800 g of a solvent mixture comprising methylene chloride and ethanol. The solvent is removed in vacuo and the remaining material is communicated.

Granules II 200 g of nifedipine are mixed with 400 g of microcrystalline cellulose and 240 g of corn starch and granulated with a paste of 30 g of corn starch in water. The moist composition is dried and screened.

Granules I and II are mixed with 126 g of crosslinked PVP and 4 g of magnesium stearate, and an amount of 210 g is filled into hard gelatin capsules.

In a variant of this example, 210 g of this mixture of granules I and II are compressed to produce tablets.

EXAMPLE 5

Granules I 100 g of nifedipine and 600 g of hydroxypropylmethylcellulose are dissolved in 500 g of a solvent mixture comprising methylene chloride and ethanol. The solvent is removed in vacuo and the remaining material is comminuted.

Granules II 300 g of nifedipine are mixed with 400 g of microcrystalline cellulose, 360 g of corn starch and 100 g of lactose and granulated with a paste of 40 g of corn starch in water. The moist composition is dried and then screened.

Granules I and granules II are mixed with 96 g of sodium carboxymethylcellulose and 4 g of magnesium stearate, and an amount of 200 g is filled into hard gelatin capsules or compressed to produce tablets.

EXAMPLE 6

Granules I 50 g of nifedipine and 150 g of PVP 25 are dissolved in 400 g of acetone, and this solution is granulated with a mixture of 500 g of microcrystalline cellose, 160 g of corn starch and 40 g of crosslinked PVP. The composition is dried and screened.

Granules II 200 g of nifedipine are mixed with 200 g of microcrystalline cellulose and 240 g of corn starch and granulated with a paste of 30 g of corn starch in water. The moist composition is dried and screened. Granules I and granules Ii are mixed with 126 g of crosslinked PVP and 4 g of magnesium stearate, and an amount of 170 mg is filled into hard gelatin capsules or compressed to produce tablets.

EXAMPLE 7

Granules I 50 g of nifedipine and 200 g of PVP 25 are dissolved in 400 g of acetone, and this solution is granulated with a mixture of 350 g of microcrystalline cellulose, 40 g of corn starch and 25 g of crosslinked PVP. The composition is dried and screened.

Granules II

The preparation of granules II is carried out in the same manner as in Example 2.

Granules I and II are mixed with 129.5 g of crosslinked PVP and 3 g of magnesium stearate, and the mixture is compressed to produce tablets each weighing 130 mg.

It is understood that the specification and examples are illustrative but not limitative of the present invention and that other embodiments within the spirit and scope of the invention will suggest themselves to those skilled in the art.

We claim:

1. A solid two-phase medicament formulation comprising a nifedipine coprecipitate, in which the nifedipine is present in a non-crystalline form, and crystalline nifedipine.

2. A two-phase medicament formulation according to claim 1, comprising a nifedipine coprecipitate, in which about 1 part by weight of nifedipine is present in a dissolved, non-crystalline form in about 1 to 10 parts by weight of coprecipitate former, and about 1 to 5 parts by weight of crystalline nifedipine.

3. A two-phase medicament formulation according to claim 1, in the form of tablets, coated tablets or hard gelatin capsules containing a nifedipine coprecipitate which comprises of 1 part by weight of nifedipine and about 1 to 10 parts by weight of a coprecipitate former.

4. A two-phase medicament formulation according to claim 3, wherein the nifedipine coprecipitate contains about 2 to 6 parts by weight of the coprecipitate former.

5. A two-phase medicament formulation according to claim 1, where the coprecipitate former is selected from the group comprising polyvinylpyrrollidone, methylcellulose, hydroxypropylcellulose and hydroxypropylmethylcellulose.

6. A two-phase medicament formulation according to claim 1, where the crystalline nifedipine has a mean particle diameter of about 10 to 1 μm.

7. A two-phase medicament formulation according to claim 6, wherein the nifedipine crystals have a specific surface area of about 1.0 to 4.0 m$^2$/g.

8. A two-phase medicament formulation according to claim 2, wherein the coprecipitate former comprises polyvinylpyrrolidone.

9. In the treatment of cardiovascular and coronary disorders by administering to a patient suffering therefrom a solid preparation comprising nifedipine, the improvement which comprises administering such nifedipine in the form of a formulation according to claim 1, whereby the nifedipine rapidly enters the blod stream in a relatively high concentration which is maintained for a relatively long time.

* * * * *